US008730466B2

(12) United States Patent
Ashmead et al.

(10) Patent No.: US 8,730,466 B2
(45) Date of Patent: May 20, 2014

(54) OPTICAL SPECTROMETER WITH UNDERFILLED FIBER OPTIC SAMPLE INTERFACE

(75) Inventors: Damian W. Ashmead, Belleville, WI (US); Francis J. Deck, Madison, WI (US)

(73) Assignee: Thermo Electron Scientific Instruments LLC, Madison, WI (US)

( * ) Notice: Subject to any disclaimer, the term of this patent is extended or adjusted under 35 U.S.C. 154(b) by 224 days.

(21) Appl. No.: 13/183,346

(22) Filed: Jul. 14, 2011

(65) Prior Publication Data

US 2013/0016348 A1  Jan. 17, 2013

(51) Int. Cl.
*G01N 21/01* (2006.01)
*G01J 3/28* (2006.01)

(52) U.S. Cl.
USPC .......................................... 356/244; 356/326

(58) Field of Classification Search
USPC ................................................ 356/244, 326
See application file for complete search history.

(56) References Cited

U.S. PATENT DOCUMENTS

| 5,245,682 | A | 9/1993 | Ortiz, Jr. | |
| 6,950,182 | B1* | 9/2005 | Liphardt et al. | 356/237.1 |
| 2005/0020892 | A1 | 1/2005 | Acosta et al. | |
| 2008/0174768 | A1* | 7/2008 | Belz | 356/73 |
| 2009/0051910 | A1* | 2/2009 | Imura | 356/243.8 |
| 2009/0059225 | A1 | 3/2009 | Robertson et al. | |
| 2009/0103077 | A1 | 4/2009 | Robertson, Jr. et al. | |
| 2009/0213882 | A1 | 8/2009 | Weida et al. | |
| 2009/0316150 | A1 | 12/2009 | Myrick et al. | |
| 2010/0060879 | A1 | 3/2010 | Large et al. | |
| 2010/0134802 | A1* | 6/2010 | Chan et al. | 356/497 |
| 2010/0165339 | A1* | 7/2010 | Morgan et al. | 356/318 |
| 2010/0208261 | A1 | 8/2010 | Sens et al. | |
| 2011/0112377 | A1 | 5/2011 | Papac et al. | |

FOREIGN PATENT DOCUMENTS

GB  2318412 A  4/1998

OTHER PUBLICATIONS

Insertion Loss and Link Loss Testing, Tempo, A Textron Company, 257A | 850nm LED Source, Data Sheet, 2003.
Simard et al., 092 Understanding Launch Conditions for Multimode Connector and Cable-Assembly Testing, Application Note, www.exfo.com, May 2002.

* cited by examiner

*Primary Examiner* — Kara E. Geisel
*Assistant Examiner* — Hina F Ayub
(74) *Attorney, Agent, or Firm* — Michael C. Staggs

(57) ABSTRACT

An optical device is provided that includes a converging lens device, a transmitting optical fiber, a sample holder, and a receiving optical fiber. The converging lens device focuses light onto the transmitting optical fiber, which receives the focused light through an entrance face and transmits the light from an exit face, through a sample, and onto the receiving optical fiber. The sample holder holds the sample for analysis. The receiving optical fiber receives the light through an entrance face of the receiving optical fiber after transmission through the sample. The converging lens device is positioned to focus the light onto the entrance face of the transmitting optical fiber such that a half-angle of the angular distribution of the focused light that reaches the entrance face of the transmitting optical fiber is selected to underfill an entrance aperture of the entrance face of the receiving optical fiber in both a spatial dimension and an angular dimension.

16 Claims, 12 Drawing Sheets

OPTICAL SPECTROMETER WITH UNDERFILLED FIBER OPTIC SAMPLE INTERFACE

BACKGROUND

Optical spectrometers measure the intensity of light at one or more wavelengths to determine certain characteristics of samples, usually liquid samples. The light, usually in the ultraviolet (UV) and/or visible (Vis) wavelength ranges though other wavelength ranges may be used including the near-infrared (NIR) and infrared (IR) wavelengths ranges, is directed through a sample, and the intensity of the output light at the one or more wavelengths is compared to the intensity of the input light at the one or more wavelengths to determine the characteristics of the sample, such as the absorbance, the transmittance, the fluorescence, and/or the reflectance. The measured characteristics provide information about the identity of the components within the sample, their relative concentrations, and possibly other features of the sample. Optical spectrometers are becoming increasingly popular for analysis of small specimens, such as those having a volume of two microliters (μl) or less based on their value in the fields of biotechnology and pharmacology, where specimens often tend to be available in very limited quantities.

In spectroscopy, optical fibers may be used to transmit the light through the sample in order to analyze the composition of the sample. The optical fiber may include a single fiber or a bundle of multiple fibers. Optical fiber typically consists of a transparent core surrounded by a transparent cladding material with a lower index of refraction. The light is kept in the core by total internal reflection causing the fiber to act as a waveguide. There is a maximum angle from the optical fiber axis at which light may enter an entrance face of the optical fiber, propagate in the core of the fiber, and exit an exit face of the optical fiber. The sine of this maximum angle is the numerical aperture (NA) of the optical fiber. As a result of the maximum angle, different distributions of light transmitted into an optical fiber can result in different intensity measurements out of the optical fiber.

The launch spot size is the area of the optical fiber face that is illuminated by the light from the light source. The diameter of the launch spot depends on the size and positioning of the light source and the properties of the optical elements, such as lenses, between the light source and the entrance face of the optical fiber. The angular distribution is the angular extent of the light from the optical light source incident on the entrance face of the optical fiber. The angular distribution also depends on the size and positioning of the light source and the properties of the optical elements between the light source and the entrance face of the optical fiber. As a result, relative to the optical fiber, the light distribution that is created by the light source and any intervening optical elements and that enters the optical fiber can be defined as the statistical distribution of the light in four degrees of freedom, two spatial and two angular.

Multimode optical fiber launch conditions are typically characterized as being underfilled or overfilled. An underfilled optical fiber concentrates most of the optical power in the center of the optical fiber. An underfilled launch results when the launch core diameter and the angular distribution are smaller than that of the optical fiber core.

UV-Vis spectroscopy generally measures the absorption or reflectance of a sample in the ultraviolet-visible spectral region, and thus, uses light in the visible and adjacent (near-UV and NIR) ranges. The absorption or reflectance in the visible range directly affects the perceived color of the chemicals involved. The Beer-Lambert law states that the absorbance of a sample is directly proportional to the concentration of the absorbing species in the sample and the path length. Thus, for a fixed path length, UV/Vis spectroscopy can be used to determine the concentration of the absorber in the sample. It is necessary to know how quickly the absorbance changes with the concentration of the absorber in the sample. As examples, this can be taken from references (tables of molar extinction coefficients), or determined using a calibration curve.

The optical spectrometer measures the intensity of light passing through a sample and compares it to the intensity of light before it passes through the sample. The ratio is called the transmittance. A variety of light sources may be used to perform spectroscopy, such as UV-Vis spectroscopy, though the wavelength of the light source is selected based on the type of components to identify in a sample. For example, the optical spectrometer may utilize a light emitting diode (LED) or a variety of different types of lamps, such as a Tungsten filament, a deuterium arc lamp, and a Xenon arc lamp, etc. as the light source.

The rated lifetime of an LED is given in terms of how long it takes to reach half of its initial intensity. As a result, the fluctuation over the lifetime of the LED is expected to be substantial. In addition, the intensity of the LED may vary as a function of ambient or internal temperature of the instrument with time scales on the order of minutes. Therefore, successive analytical values, measured over a period of minutes to hours, may show noticeable time dependencies that exceed acceptable limits for a useful optical spectrometer. Drift is a change in the reported analytical value of the intensity of the LED over time and may result even when the optical spectrometer is undisturbed. It has been found that different wavelength LEDs may drift at different rates and in different directions and different portions of each LED may themselves drift at different rates with the result that no two optical spectrometers drift identically.

In addition to drift, other factors may cause variation in the intensity values measured by the optical spectrometer. For example, contamination on one or both of the optical fibers may cause variations. Opaque or scattering inclusions in the sample, including dust, particulates, and air bubbles may cause variations. Misplacement of the sample drop on the optical fiber interface, for example due to the normal variation based on manual operation, may cause variations.

The conventional path length for UV-Vis transmission spectroscopy is one centimeter (cm). Thus, there is a 1:1 relationship between absorbance and absorptivity when the latter is reported in units of absorbance per cm. For microliter samples, the path length is much smaller, on the order of 0.005 to 0.02 cm. Thus, absorbance measurements have to be multiplied by large values (50 to 200 times) to report the absolute absorbance in the conventional units expected by users. This factor also multiplies errors in the absorbance measurement making error correction associated with the variations in intensity important design criteria in the manufacture of optical spectrometers, particularly those that utilize an LED light source.

SUMMARY

In an illustrative embodiment, an optical device for analyzing a sample is provided. The optical device includes, but is not limited to, a converging lens device, a transmitting optical fiber, a sample holder, and a receiving optical fiber. The converging lens device is mounted to receive light that is substantially collimated and is configured to focus the received light onto the transmitting optical fiber. The transmitting optical fiber includes an entrance face and an exit face and is mounted to receive the focused light through the entrance face and to transmit the received, focused light from the exit face, through the sample, and onto the receiving optical fiber. The sample holder is configured to hold the sample for analysis. The receiving optical fiber includes an entrance face and an exit face and is mounted to receive the transmitted light through the entrance face of the receiving optical fiber after transmission through the sample. The converging lens device is positioned to focus the received light onto the entrance face of the transmitting optical fiber such that a half-angle of the angular distribution of the focused light that reaches the entrance face of the transmitting optical fiber is selected to underfill an entrance aperture of the entrance face of the receiving optical fiber in both a spatial dimension and an angular dimension.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

DETAILED DESCRIPTION

Figure 1:
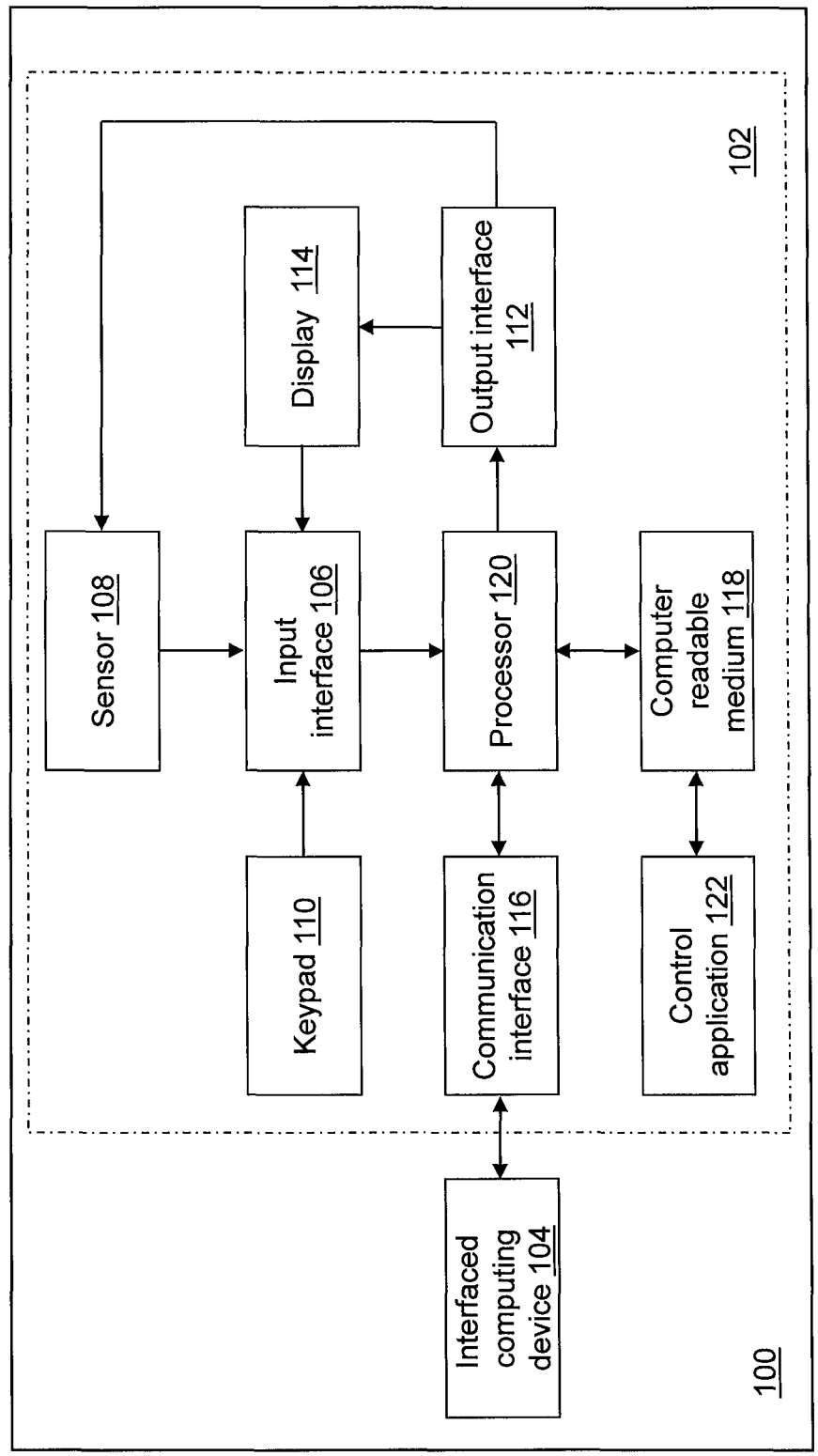
FIG. 1 depicts a block diagram of a spectroscopy system in accordance with an illustrative embodiment.

With reference to FIG. 1, a block diagram of a spectroscopy system 100 is shown in accordance with an illustrative embodiment. In an illustrative embodiment, spectroscopy system 100 may include a spectrometer 102 and an interfaced computing device 104 to which spectrometer 102 may be connected. Spectrometer 102 may not connect to interfaced computing device 104. If connected, spectrometer 102 and interfaced computing device 104 may be connected directly or through a network. The network may be any type of wired and/or wireless public or private network including a cellular network, a local area network, a wide area network such as the Internet, etc. Spectrometer 102 may send and receive information to/from interfaced computing device 104. For example, spectrometer 102 may send results obtained for a sample for storage on interfaced computing device 104. As another example, spectrometer 102 may receive software updates from interfaced computing device 104. Interfaced computing device 104 may include a computing device of any form factor such as a personal digital assistant, a desktop computer, a laptop computer, an integrated messaging device, a cellular telephone, a smart phone, a pager, etc. without limitation.

Spectrometer 102 may include an input interface 106, a sensor 108, a keypad 110, an output interface 112, a display 114, a communication interface 116, a computer-readable medium 118, a processor 120, and a control application 122. Different and additional components may be incorporated into spectrometer 102. For example, a battery, such as a lithium ion battery, may provide power for the various components of spectrometer 102.

Input interface 106 provides an interface for receiving information from the user for entry into spectrometer 102 as known to those skilled in the art. Input interface 106 may use various input technologies including, but not limited to, a keyboard, a pen and touch screen, a mouse, a track ball, a touch screen, keypad 110, one or more buttons, etc. to allow the user to enter information into spectrometer 102 or to make selections presented in a user interface displayed on display 114. Input interface 106 further may provide an interface for receiving information from sensor 108 for entry into spectrometer 102 as known to those skilled in the art. In the illustrative embodiment, sensor 108 measures the intensity of light at one or more wavelengths, for example at 260 and 280 nanometers (nm), which are of interest for protein and DNA concentration determinations, to determine the absorbance of liquid samples. Spectrometer 102 may have one or more input interfaces that use the same or a different input interface technology.

Output interface 112 provides an interface for outputting information for review by a user of spectrometer 102. For example, output interface 112 may include an interface to display 114, a speaker, a printer, etc. Display 114 may be a thin film transistor display, a light emitting diode display, a liquid crystal display, or any of a variety of different displays known to those skilled in the art. Spectrometer 102 may have one or more output interfaces that use the same or a different interface technology. The same interface may support both input interface 106 and output interface 112. For example, a touch screen both allows user input and presents output to the user. Display 114, the speaker, and/or the printer further may be accessible to spectrometer 102 through communication interface 116.

Communication interface 116 provides an interface for receiving and transmitting data between devices using various protocols, transmission technologies, and media as known to those skilled in the art. Communication interface 116 may support communication using various transmission media that may be wired or wireless. Spectrometer 102 may have one or more communication interfaces that use the same or a different communication interface technology. Data and messages may be transferred between spectrometer 102 and interfaced computing device 104 using communication interface 116.

Computer-readable medium 118 is an electronic holding place or storage for information so that the information can be accessed by processor 120 as known to those skilled in the art. Computer-readable medium 118 can include, but is not limited to, any type of random access memory (RAM), any type of read only memory (ROM), any type of flash memory, etc. such as magnetic storage devices (e.g., hard disk, floppy disk, magnetic strips, . . . ), optical disks (e.g., CD, DVD, . . . ), smart cards, flash memory devices, etc. Spectrometer 102 may have one or more computer-readable media that use the same or a different memory media technology. Spectrometer 102 also may have one or more drives that support the loading of a memory media such as a CD or DVD. Computer-readable medium 118 may provide the electronic storage medium for a database that stores information for use by control application 122 in the operation of sensor 108.

Processor 120 executes instructions as known to those skilled in the art. The instructions may be carried out by a special purpose computer, logic circuits, or hardware circuits. Thus, processor 120 may be implemented in hardware, firmware, or any combination of these methods and/or in combination with software. The term "execution" is the process of running an application or the carrying out of the operation called for by an instruction. The instructions may be written using one or more programming language, scripting language, assembly language, etc. Processor 120 executes an instruction, meaning that it performs/controls the operations called for by that instruction. Processor 120 operably couples with output interface 112, with input interface 106, with computer-readable medium 118, and with communication interface 116 to receive, to send, and to process information. Processor 120 may retrieve a set of instructions from a permanent memory device and copy the instructions in an executable form to a temporary memory device that is generally some form of RAM. Spectrometer 102 may include a plurality of processors that use the same or a different processing technology.

Control application 122 performs operations associated with controlling, maintaining, updating, etc. the operation of sensor 108 with possible user input. Some or all of the operations described herein may be embodied in control application 122. The operations may be implemented using hardware, firmware, software, or any combination of these methods. With reference to the example embodiment of FIG. 1, control application 122 is implemented in software (comprised of computer-readable and/or computer-executable instructions) stored in computer-readable medium 118 and accessible by processor 120 for execution of the instructions that embody the operations of control application 122. Control application 122 may be written using one or more programming languages, assembly languages, scripting languages, etc.

Figure 2:
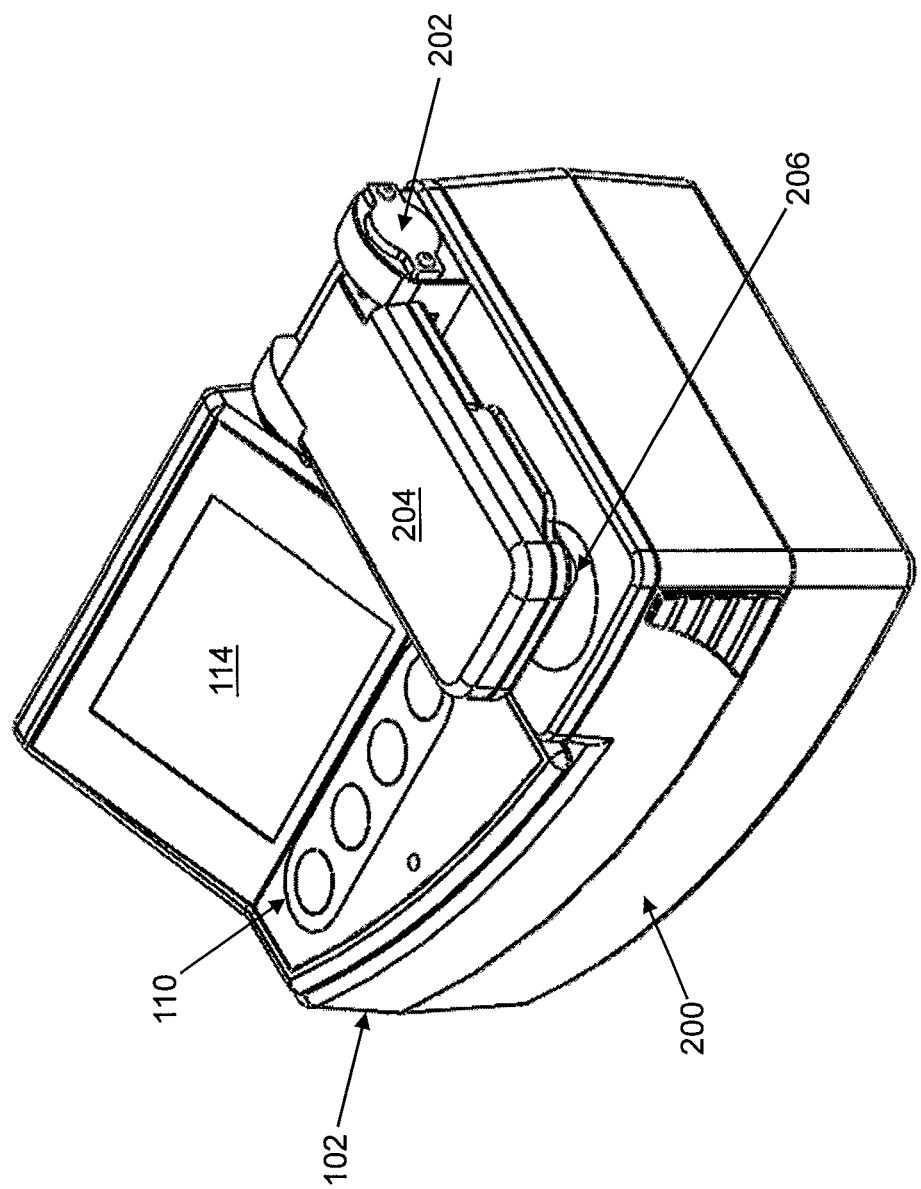
FIG. 2 depicts a perspective view of a spectrometer in accordance with an illustrative embodiment.

With reference to FIG. 2, a perspective view of spectrometer 102 is shown in accordance with an illustrative embodiment. The components of spectrometer 102 are mounted within or to a housing 200 and may be arranged in a variety of manners. As used in this disclosure, the term "mount" includes join, unite, connect, associate, insert, hang, hold, affix, attach, fasten, bind, paste, secure, bolt, screw, rivet, solder, weld, glue, form over, layer, and other like terms. The phrases "mounted on" and "mounted to" include any interior or exterior portion of the element referenced. Display 114 and keypad 110 may be mounted on housing 200 for ease of access by a user. Additionally, a hinge 202 is mounted to housing 200. A sensor arm 204 is mounted to hinge 202 for rotational movement of sensor arm 204 away from a sample holder 206 of sensor 108. Other mechanisms may be used to allow movement of sensor arm 204 away from sample holder 206 so that a sample can be placed on or in sample holder 206 for analysis.

Figure 3:
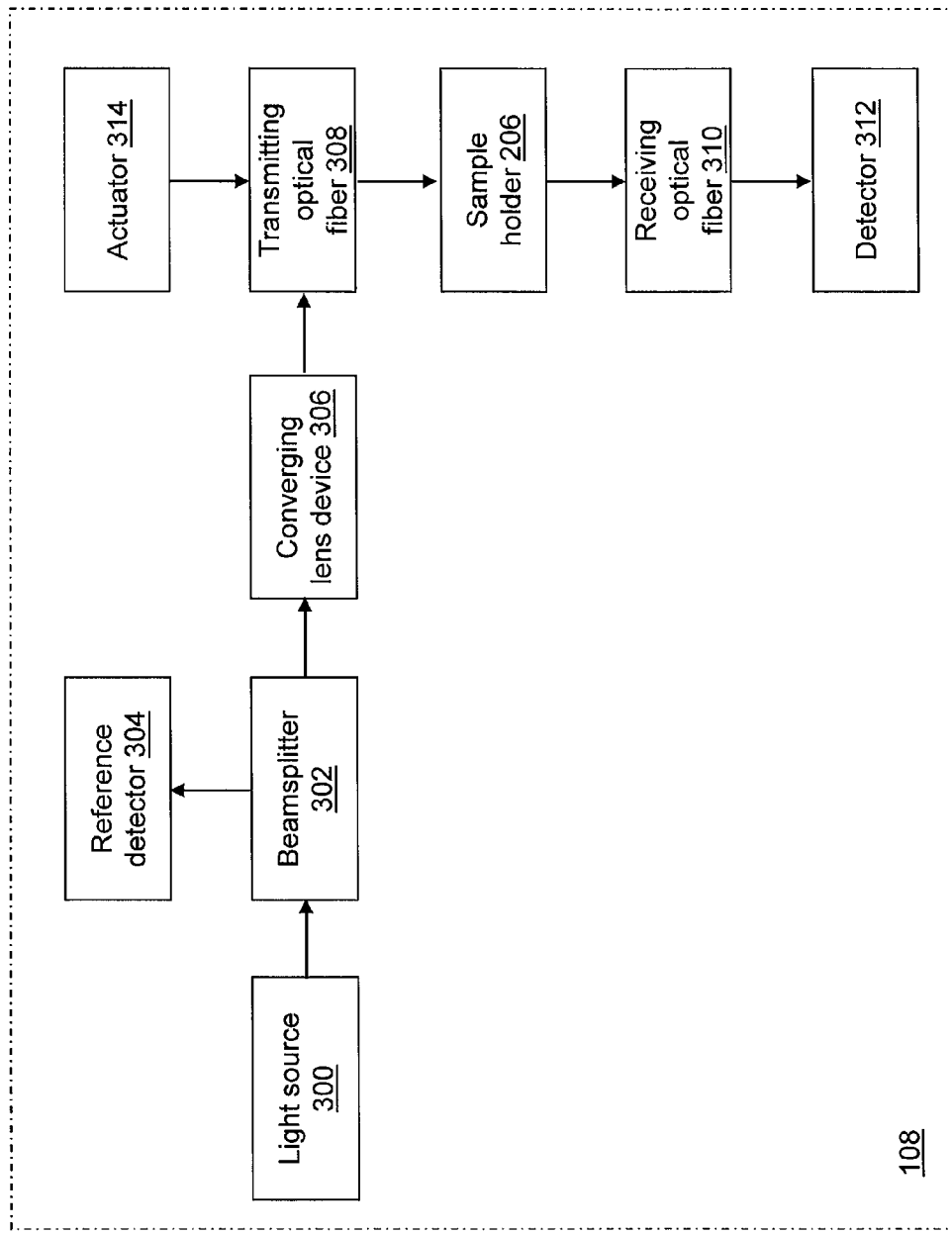
FIG. 3 depicts a block diagram of a sensor incorporated in the spectrometer of FIG. 2 in accordance with an illustrative embodiment.

With reference to FIG. 3, a block diagram of sensor 108 is shown in accordance with an illustrative embodiment. In the illustrative embodiment, sensor 108 may include, but is not limited to, a light source 300, a beamsplitter 302, a reference detector 304, a converging lens device 306, a transmitting optical fiber 308, sample holder 206, a receiving optical fiber 310, a detector 312, and an actuator 314. Light source 300 may include one or more light sources that emit light approximately centered at one or more wavelengths selected for analysis of the sample placed on or in sample holder 206. In an illustrative embodiment, light source 300 emits light that is substantially collimated and that may be centered at a plurality of different wavelengths.

Beamsplitter 302 is positioned and configured to reflect a reference portion of light emitted by light source 300 toward reference detector 304. Beamsplitter 302 may include various optical devices such as a partly transmissive mirror as known to those of skill in the art. Beamsplitter 302 further may be selected to reflect various amounts of the light emitted by light source 300 dependent on the amount of power needed to form a measurement by reference detector 304. In an illustrative embodiment, beamsplitter 302 includes a plate of fused silica held at an angle to reflect approximately 10% of the light emitted by light source 300 toward reference detector 304.

Reference detector 304 is configured to generate a reference signal indicating an intensity of the reference portion of light to determine the unattenuated power level of the light emitted by light source 300. In an illustrative embodiment, reference detector 304 includes a silicon photodiode though other detectors may be used.

Converging lens device 306 is positioned to receive the light emitted by light source 300 and configured to focus the received light onto transmitting optical fiber 308. As will be discussed in more detail relative to FIGS. 10 and 11, converging lens device 306 is further positioned to focus the received light spatially and angularly onto a core portion of an entrance face 502 (shown with reference to FIG. 5) of transmitting optical fiber 308 such that a half-angle of the angular distribution of the focused light relative to entrance face 502 of transmitting optical fiber 308 is selected to underfill an entrance aperture of an entrance face 508 (shown with reference to FIG. 5) of receiving optical fiber 310. The entrance aperture is defined both spatially and angularly.

Transmitting optical fiber 308 includes entrance face 502 and an exit face 504 (shown with reference to FIG. 5). Receiving optical fiber 310 includes entrance face 508 and an exit face 510 (shown with reference to FIG. 5). Transmitting optical fiber 308 is used to transmit the focused light through the sample held by sample holder 206 and towards receiving optical fiber 310. Receiving optical fiber 310 is used to receive the light after transmission through the sample held by sample holder 206. Transmitting optical fiber 308 and/or receiving optical fiber 310 may include a single fiber or a bundle of multiple fibers.

Sample holder 206 is configured to hold the sample for analysis. Sample holder 206 may be sized to hold various volumes of sample. In an illustrative embodiment, sample holder 206 is sized to hold sample sizes in the range of 0.25 to 20 microliters (μl). In illustrative embodiments, sample holder 206 is a sample pedestal or a cuvette made of glass, plastic, quartz, etc.

Detector 312 receives the light transmitted through the sample and received and propagated through receiving optical fiber 310. Detector 312 converts the received light into an electrical signal indicating an intensity of the received light after transmission through the sample. In an illustrative embodiment, detector 312 includes a photodiode detector.

Actuator 314 may be used to control translational and/or rotational movement of one or more components of sensor 108. Exemplary actuators include an electric motor, a servo, stepper, or piezo motor, a pneumatic actuator, a gas motor, or the like. For example, actuator 314 may be coupled to control movement of transmitting optical fiber 308 and/or receiving optical fiber 310 to adjust a distance or path length between exit face 504 of transmitting optical fiber 308 and entrance face 508 of receiving optical fiber 310. In an illustrative embodiment, actuator 314 is coupled to control movement of transmitting optical fiber 308.

Various components of sensor 108 may be operably coupled to processor 120 to receive information from processor 120 and/or to send information to processor 120 under control of control application 122. For example, processor 120 is operably coupled to light source 300 to control the switching on or off of the one or more light sources of light source 300. Processor 120 also may be operably coupled to reference detector 304 and detector 312 to receive the electrical signals generated by each detector. Processor 120 further may be operably coupled to actuator 314 to control adjustment of the distance between exit face 504 of transmitting optical fiber 308 and entrance face 508 of receiving optical fiber 310. Processor 120 determines the absorbance of the sample based on the electrical signals generated by each detector 304, 312. Processor 120 further may signal reference detector 304 and detector 312 to generate the electrical signals based on the on or off operation of light source 300. Processor 120 may produce an output signal indicating a value of the absorbance of the sample on display 114 and/or transmit the value with other related information to interfaced computing device 104. Processor 120 further may control the collection of multiple readings for the sample, for example, at different wavelengths or for different path lengths.

To use spectrometer 102, a user may rotate sensor arm 204 away from sample holder 206 and place a drop of the sample on or in sample holder 206. For example, the user may use a pipette to place the drop of the sample on sample holder 206. The user may rotate sensor arm 204 toward sample holder 206 after placement of the drop on sample holder 206. One or more of these operations may be automated.

Intensity measurements may be initiated by selecting, for example, a button on keypad 110 or a button indicator on display 114 that triggers initiation of a measurement sequence under control of control application 122. After positioning adjacent the sample, rotating sensor arm 204 is moved into the position as shown with reference to FIGS. 4, 5a, and 5b.

Electrical signals indicating the intensity detected at both reference detector 304 and detector 312 is received with light source 300 turned on and turned off. The reported absorbance for a given wavelength of light source 300 may be calculated as $$A = -\log[(I_{sample\ on} - I_{sample\ off})/(I_{reference\ on} - I_{reference\ off})] \quad (1)$$

where $I_{sample\ on}$ is the intensity measured at detector 312 with light source 300 emitting light, $I_{sample\ off}$ is the intensity measured at detector 312 with light source 300 off, $I_{reference\ on}$ is the intensity measured at reference detector 304 with light source 300 emitting light, and $I_{reference\ off}$ is the intensity measured at reference detector 304 with light source 300 off. Thus, use of reference detector 304 allows correction for variations in light source 300. In an illustrative embodiment, the electrical signal associated with the intensity measurement is a current measurement from reference detector 304 and from detector 312.

In an illustrative embodiment, control application 122 further initiates a differential measurement, which is a technique for measuring absorptivity, where absorbance measurements are made for two path lengths which are subtracted to yield a single absorbance value and which can be converted to absorptivity by dividing by the path length difference. Samples can also be measured with a differential absorbance path. For example, sample absorbance can be measured by changing the optical path length (sample height) over which the absorbance is measured, measuring the sample at each of the one or more path lengths, where the difference in path length combined with the difference in transmitted intensity can be used to calculate the sample absorbance. This can be of significant value if the sample is highly absorbing and the accuracy of the path difference for a small path difference can be better determined than the absolute full optical path. Measurements may be taken with a relatively long path and with a relatively short path length between exit face 504 of transmitting optical fiber 308 and entrance face 508 of receiving optical fiber 310. If the absorbance at the shorter path is subtracted from the absorbance of one or more of the longer paths, the absorbance of the sample can be calculated. Thus, actuator 314 may be operably coupled to either or both of transmitting optical fiber 308 and receiving optical fiber 310 to adjust the path length under control of control application 122. In an illustrative embodiment, the path lengths may be adjusted between approximately zero (touching) to approximately one mm.

Figure 4:
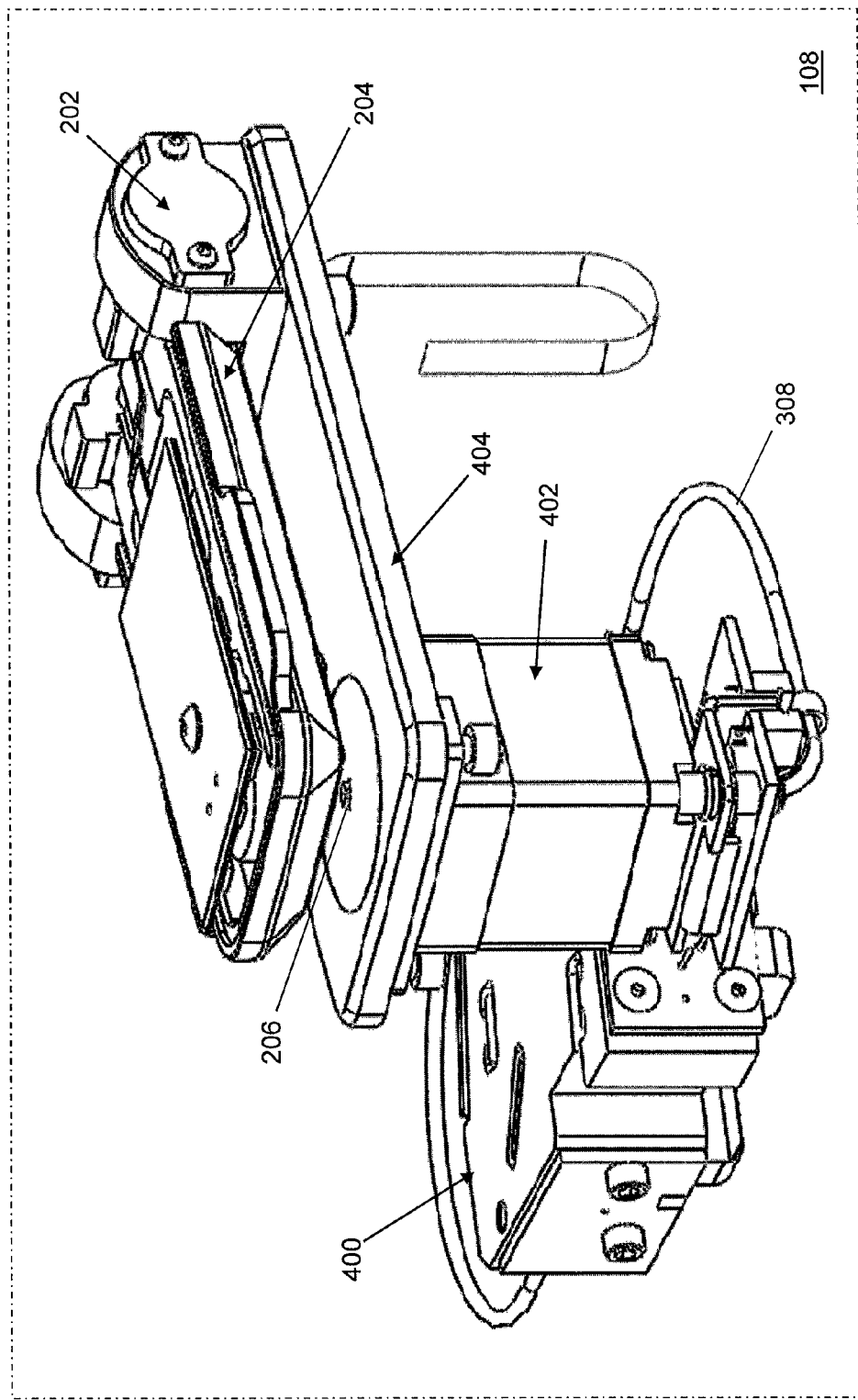
FIG. 4 depicts a perspective view of the sensor of FIG. 3 in accordance with an illustrative embodiment.

With reference to FIG. 4, a perspective view of sensor 108 is shown in accordance with an illustrative embodiment. A first housing 400 may house light source 300, beamsplitter 302, reference detector 304, converging lens device 306, and a first portion 700 (shown with reference to FIG. 7) of transmitting optical fiber 308. A second housing 402 may house a second portion 500 (shown with reference to FIG. 5) of transmitting optical fiber 308 and actuator 314. Sample holder 206 may be mounted within a platform 404 in a variety of manners as understood by a person of skill in the art. Sensor arm 204 houses receiving optical fiber 310 and detector 312.

Figure 5A:
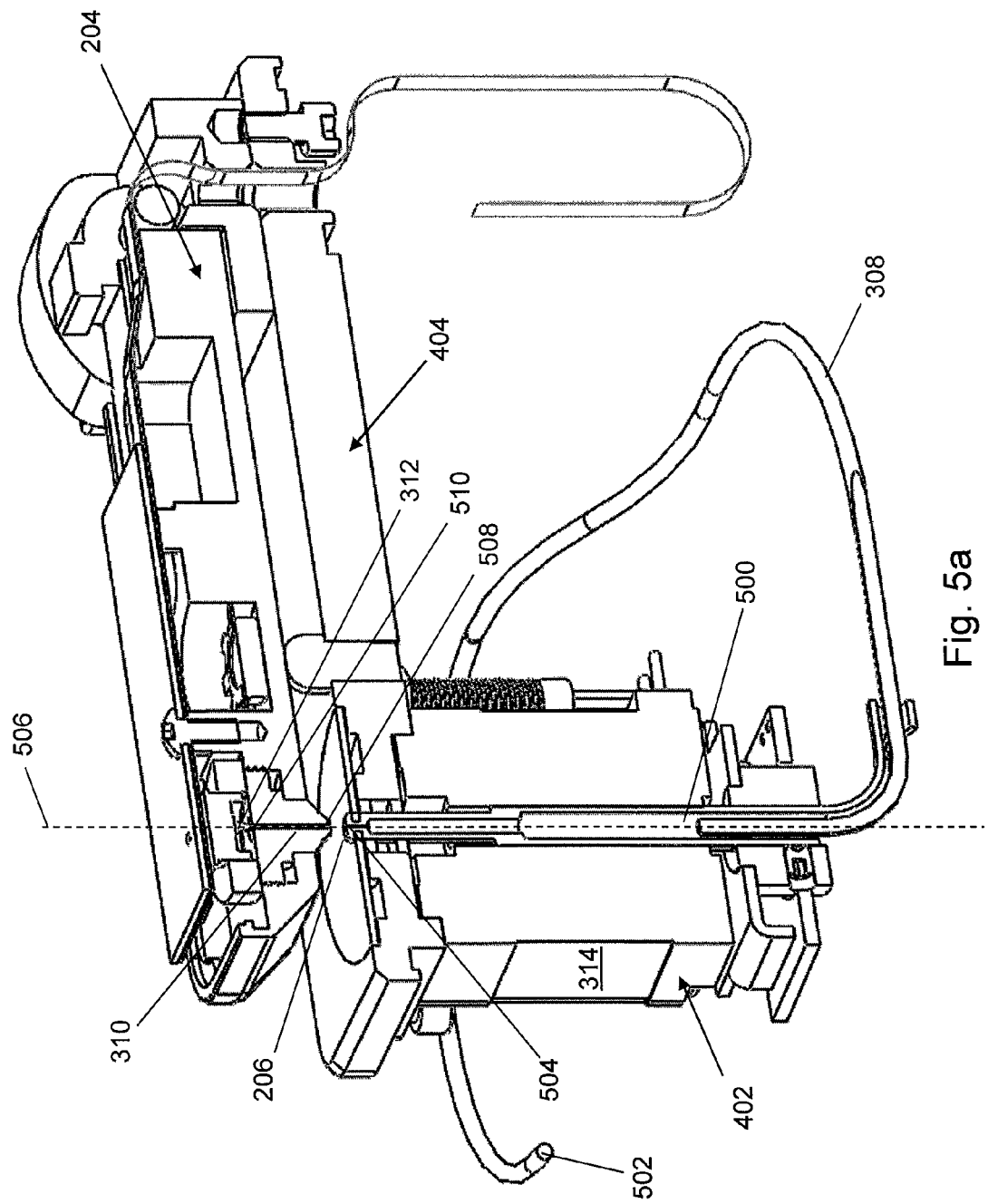
FIG. 5a depicts a cutaway view of a portion of the sensor of FIG. 3 in accordance with an illustrative embodiment.

With reference to FIG. 5a, a cutaway view of a portion of sensor 108 is shown in accordance with an illustrative embodiment. Actuator 314 is mounted to cause exit face 504 of transmitting optical fiber 308 to move either closer or farther away from entrance face 508 of receiving optical fiber 310 along optical axis 506. Transmitting optical fiber 308 is mounted within second housing 402 in a fixed arrangement such that transmitting optical fiber 308 does not move except under control of actuator 314.

Figure 5B:
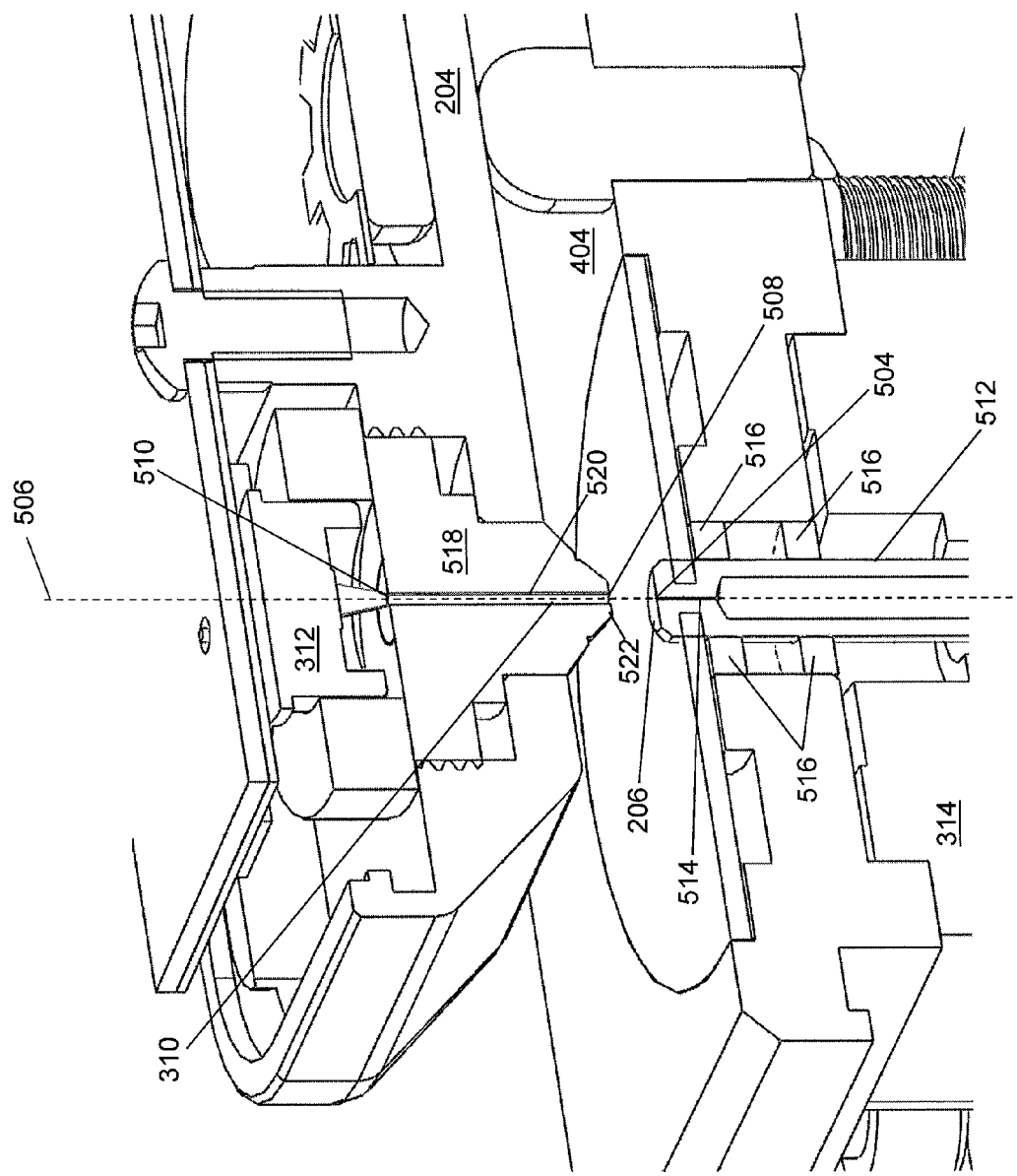
FIG. 5b depicts a zoomed view of a second portion of the sensor of FIG. 5a in accordance with an illustrative embodiment.

With reference to FIG. 5b, a zoomed view of a portion of sensor 108 of FIG. 5a is shown in accordance with an illustrative embodiment. Sensor 108 includes a lower ferrule 512 that includes a bore 514 and a polished top that forms sample holder 206. In another illustrative embodiment, sample holder 206 may include a cuvette positioned between exit face 504 of transmitting optical fiber 308 and entrance face 508 of receiving optical fiber 310. Lower ferrule 512 is centered by ring bearings 516 through which lower ferrule 512 can slide up and down. In an illustrative embodiment, at least a portion of lower ferrule 512 is threaded, and the threads engage with the rotor of actuator 314. Bore 514 of lower ferrule 512 accepts transmitting optical fiber 308. Transmitting optical fiber 308 may be held in place by adhesive. Exit face 504 of transmitting optical fiber 308 may be polished so that it is flush with sample holder 206.

Sensor 108 further includes an upper ferrule 518 that includes a bore 520. Upper ferrule 518 is mounted to sensor arm 204. Bore 520 of upper ferrule 518 accepts receiving optical fiber 310. Receiving optical fiber 310 may be held in place by adhesive and be polished so that it is flush with a contact pedestal 522 of upper ferrule 518. Contact pedestal 522 and entrance face 508 of receiving optical fiber 310 may be polished together to form a flush surface.

After placement of a sample on or in sample holder 206 and positioning of sensor arm 204, a sample "column" may be formed between exit face 504 of transmitting optical fiber 308 and entrance face 508 of receiving optical fiber 310. The column is held by capillary action between sample holder 206 and contact pedestal 522 and establishes an optical path between the optical fibers 308, 310 along an optical axis 506. Using actuator 314, different path lengths may be established between exit face 504 of transmitting optical fiber 308 and entrance face 508 of receiving optical fiber 310.

Figure 6:
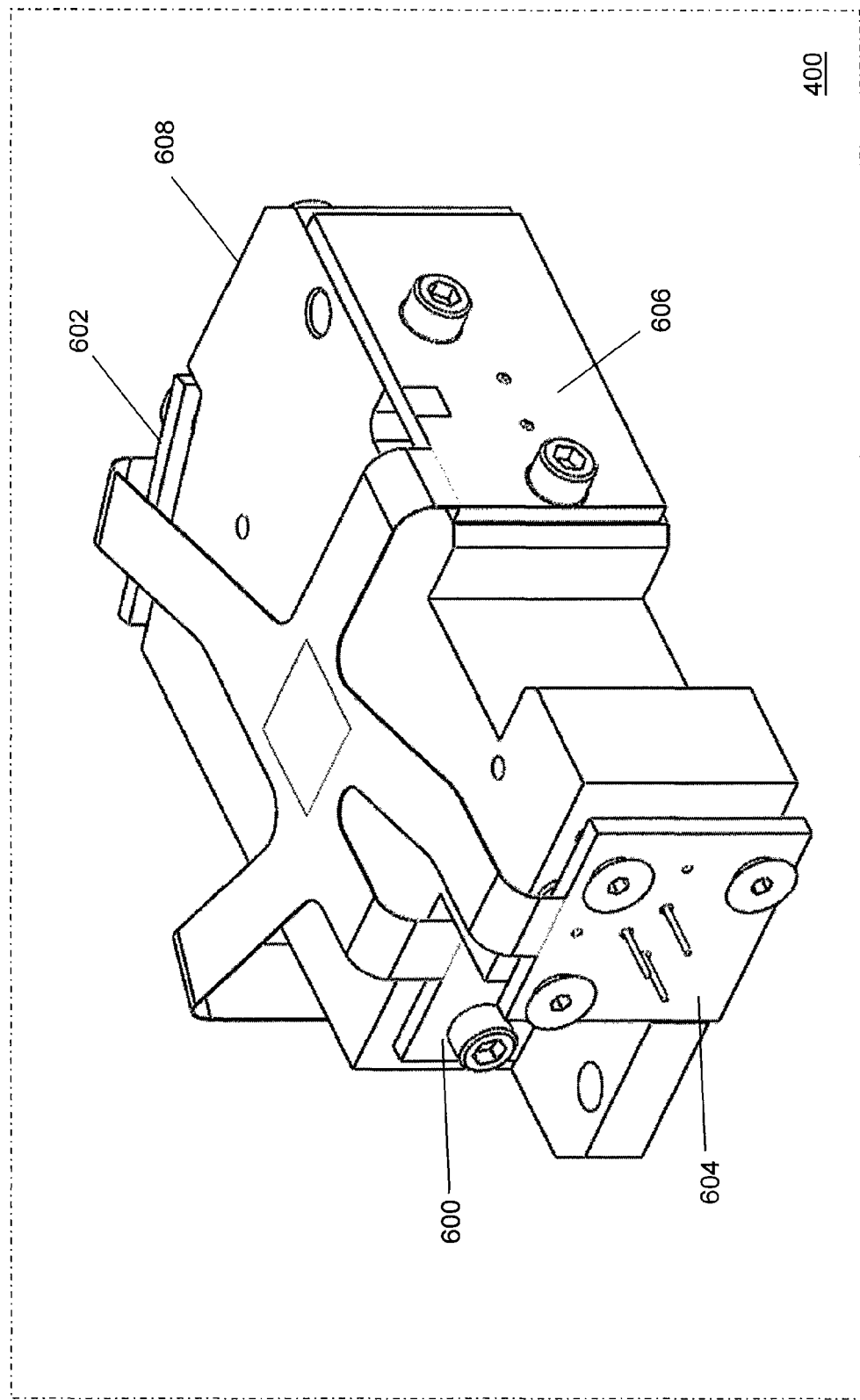
FIG. 6 depicts a perspective view of a housing which houses a light source incorporated in the sensor of FIG. 3 in accordance with an illustrative embodiment.
Figure 7:
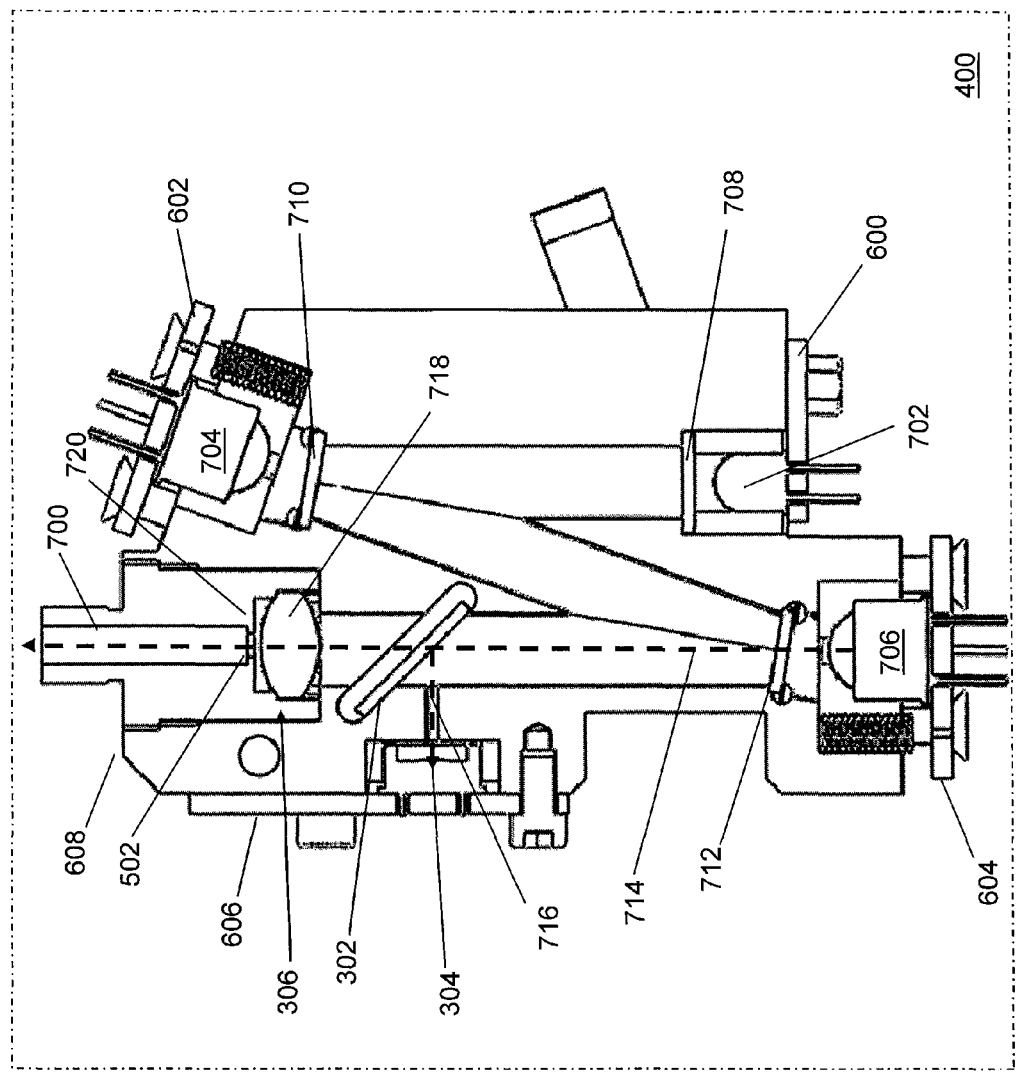
FIGS. 7-9 depict cutaway views of the housing of FIG. 6 and show light paths for different wavelength light sources in accordance with an illustrative embodiment.

With reference to FIG. 6, a perspective view of first housing 400 is shown in accordance with an illustrative embodiment. First housing 400 includes a baseline light emitting diode (LED) mounting plate 600, a first LED mounting plate 602, a second LED mounting plate 604, a reference detector mounting plate 606, and a transmitting optical fiber mounting plate 608. With reference to FIG. 7, a cutaway view of the components housed in first housing 400 is shown in accordance with an illustrative embodiment.

First housing 400 houses light source 300. In the illustrative embodiment of FIGS. 6-9, light source 300 includes a baseline LED 702, a first LED 704, and a second LED 706. Light source 300 may include a fewer or a greater number of LEDs. Additionally, light source 300 may include a variety of different types of lamps, such as a Tungsten filament, a deuterium arc lamp, and a Xenon arc lamp, etc. instead of or in addition to an LED. Light source 300 further may emit in the UV, Vis, IR, near IR, near-UV, etc. Thus, light emitted from light source 300 may not be visible.

Baseline LED mounting plate 600 mounts and fixedly positions baseline LED 702 within first housing 400. Baseline LED 702 is selected to emit baseline light approximately centered at a baseline wavelength. First LED 704 is selected to emit first light approximately centered at a first wavelength selected for analysis of the sample. Second LED 706 is selected to emit second light approximately centered at a second wavelength selected for analysis of the sample. The baseline wavelength is different from the first wavelength and the second wavelength and is selected to be centered in a region of the electromagnetic spectrum that is not used for analysis of the sample, i.e., a region of the spectrum where the analytical material of interest (the sample) does not appreciatively absorb light. In an illustrative embodiment where the sample is to be analyzed for protein and DNA, the first wavelength selected for analysis of the sample may be 280 nm, the second wavelength selected for analysis of the sample may be 260 nm, and the baseline wavelength may be selected as 365 nm. Other wavelengths within the UV, Vis, IR, near IR, and/or near-UV spectrum may be used based on the type of sample to be analyzed. In the illustrative embodiment of FIG. 7, the LEDs 702, 704, and 706 are arranged to form a beam path forming a "z" pattern though other arrangements are possible for forming the beam path between the LEDs 702, 704, and 706 and transmitting optical fiber 308. For example, different arrangements of the LEDs 702, 704, and 706 may be used in combination with different types of filters such as edge or notch filters. Thus, a variety of band limiting filters may be used.

Though the LEDs 702, 704, and 706 are centered at selected wavelengths, there may be overlap in the spectrum distribution of the light produced by the LEDs 702, 704, and 706 when part-to-part variations exceed the spectrum difference between the LEDs 702, 704, and 706. To improve the accuracy of the intensity measurements, a bandpass filter may be placed in front of one or more of the LEDs 702, 704, and 706 to filter out any emitted light from the respective LED that may overlap in wavelength with another of the LEDs 702, 704, and 706 used to form light source 300.

In the illustrative embodiment of FIG. 7, light emitted from baseline LED 702 is filtered through a baseline filter 708. Baseline filter 708 may comprise a sheet of blue filter glass such as Hoya B390 filter glass. Light emitted from first LED 704 is filtered through a first filter 710. In an illustrative embodiment where first LED 704 comprises an LED centered at a wavelength of 280 nm, first filter 710 is a bandpass filter centered at 280 nm. First filter 708 also reflects at the reference wavelength. As an example, first filter 710 may be a thin film bandpass filter that reflects wavelengths outside of its passband. Light emitted from second LED 706 is filtered through a second filter 712. In an illustrative embodiment where second LED 706 comprises an LED centered at a wavelength of 260 nm, second filter 712 is a bandpass filter centered at 260 nm. Second filter 712 also reflects at the first wavelength and at the baseline wavelength. As an example, second filter 712 may be a thin film bandpass filter that reflects wavelengths outside of its passband. In an illustrative embodiment, the passband may be six and fourteen nm though other passbands may be selected based on the cost and performance goals identified for a specific spectrometer design.

In the illustrative embodiment of FIG. 7, light from second LED 706 is filtered by second filter 712 along a first axis 714 directed toward first portion 700 of transmitting optical fiber 308. The light from second LED 706 is substantially collimated. First axis 714 is an entrance optical axis of transmitting optical fiber 308 and is perpendicular to entrance face 502 of transmitting optical fiber 308. A portion of the light is reflected by beamsplitter 302 towards reference detector 304 along a second axis 716. The remainder of the light continues along first axis 714 towards converging lens device 306 and entrance face 502 of transmitting optical fiber 308.

In the illustrative embodiment of FIG. 7, converging lens device 306 includes, but is not limited to, a converging lens 718 and an aperture plate 720. Converging lens 718 may include a fused silica lens that is biconvex or plano-convex and centered on first axis 714. Aperture plate 720 is mounted between converging lens 715 and entrance face 502 of transmitting optical fiber 308. Aperture plate 720 includes, but is not limited to, an aperture 1100 (shown with reference to FIG. 11) configured to allow a first portion of the focused light to reach entrance face 502 of transmitting optical fiber 308 and to block the remainder of the light from reaching entrance face 502 of transmitting optical fiber 308. Aperture 1100 is a hole or an opening in aperture plate 720 through which light travels. More specifically, aperture 1100 is the opening that determines the cone angle of the light that are focused onto entrance face 502 of transmitting optical fiber 308.

In an alternative embodiment, a diameter of converging lens 718 is selected to allow a portion of the light to pass through converging lens 718 and onto entrance face 502 of transmitting optical fiber 308. The remaining portion of the light is blocked by a support structure of converging lens 718 that mounts converging lens 718 within first housing 400.

Figure 8:
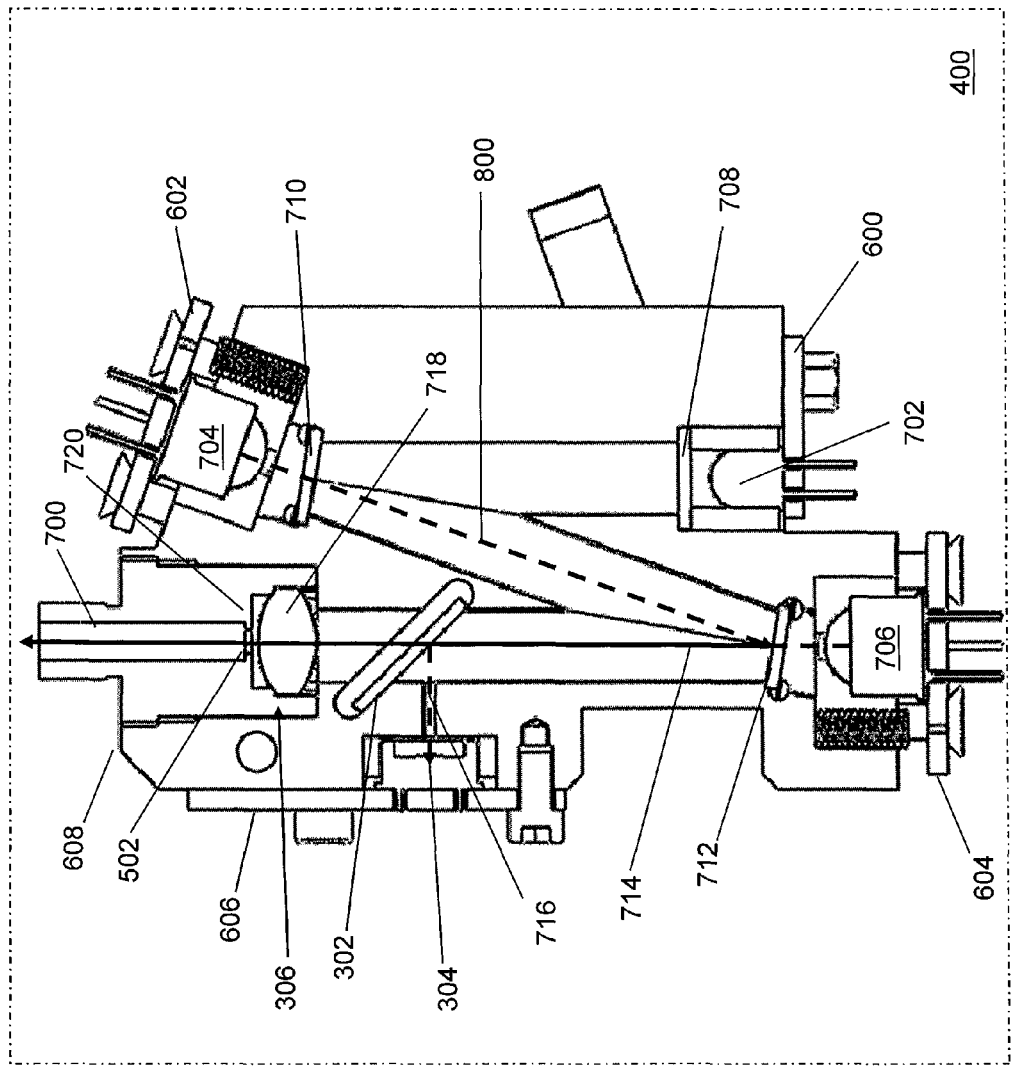

With reference to FIG. 8, second light from first LED 704 is filtered by first filter 710 along a third axis 800 directed towards second filter 712. The second light from first LED 704 is substantially collimated. Second filter 712 reflects the second light along first axis 714 towards first portion 700 of transmitting optical fiber 308. A portion of the second light is reflected by beamsplitter 302 towards reference detector 304 along second axis 716. The remainder of the second light continues along first axis 714 towards converging lens device 306 and entrance face 502 of transmitting optical fiber 308.

Figure 9:
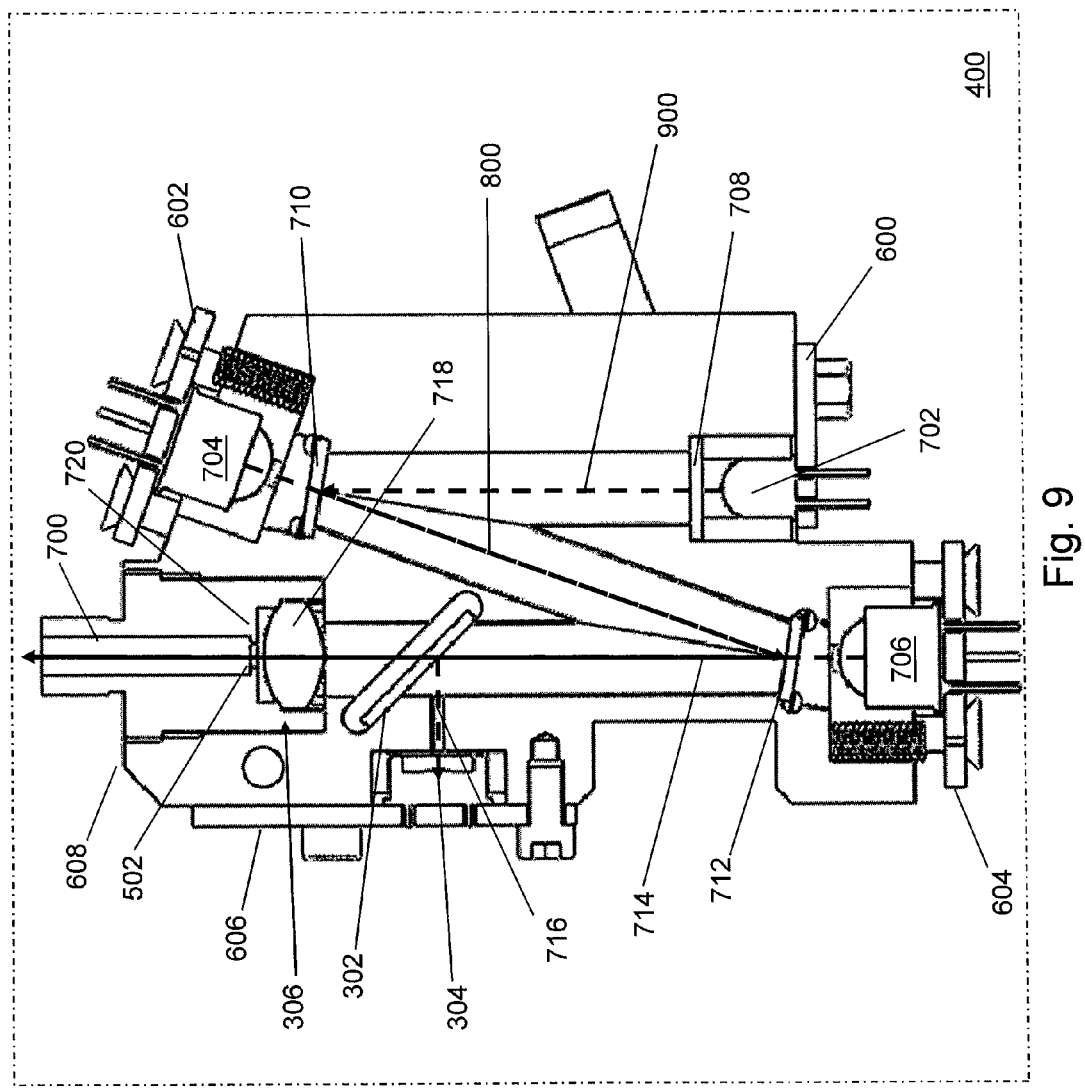

With reference to FIG. 9, third light from baseline LED 702 is filtered by baseline filter 708 along a fourth axis 900 directed towards first filter 710. The third light from baseline LED 702 is substantially collimated. First filter 710 reflects the third light along third axis 800 towards second filter 712. Second filter 712 reflects the third light along first axis 714 towards first portion 700 of transmitting optical fiber 308. A portion of the third light is reflected by beamsplitter 302 towards reference detector 304 along second axis 716. The remainder of the third light continues along first axis 714 towards converging lens device 306 and entrance face 502 of transmitting optical fiber 308.

If spectrometer 102 is configured to process multiple wavelengths, as described with reference to the illustrative embodiment of light source 300, absorbance becomes a function of wavelength. As a result, equation (1) is modified as shown below:

$$A(\lambda) = -\log\left[(I_{sample\ on}(\lambda) - I_{sample\ off})/(I_{reference\ on}(\lambda) - I_{reference\ off})\right] \quad (2)$$

where $\lambda$ is the wavelength.

The reference-corrected measurement combines absorbance values at a wavelength of interest for chemical absorbance measurement, with a "baseline" wavelength (such as that emitted by baseline LED 702), where the absorbance is expected to be independent of sample concentration, though possibly dependent on factors such as contamination on the sample holder, debris, bubbles, etc. In this case, the absorbance is computed to be:

$$A_{reported} = A(\lambda_{sample}) - A(\lambda_{baseline}) \quad (3)$$

where $A(\lambda_{sample})$ is the absorbance calculated at the wavelength of interest using equation (2) and $A(\lambda_{baseline})$ is the absorbance calculated at the baseline wavelength using equation (2). Thus, use of baseline LED 702 allows correction for factors related to contamination of the sample.

Figure 10:
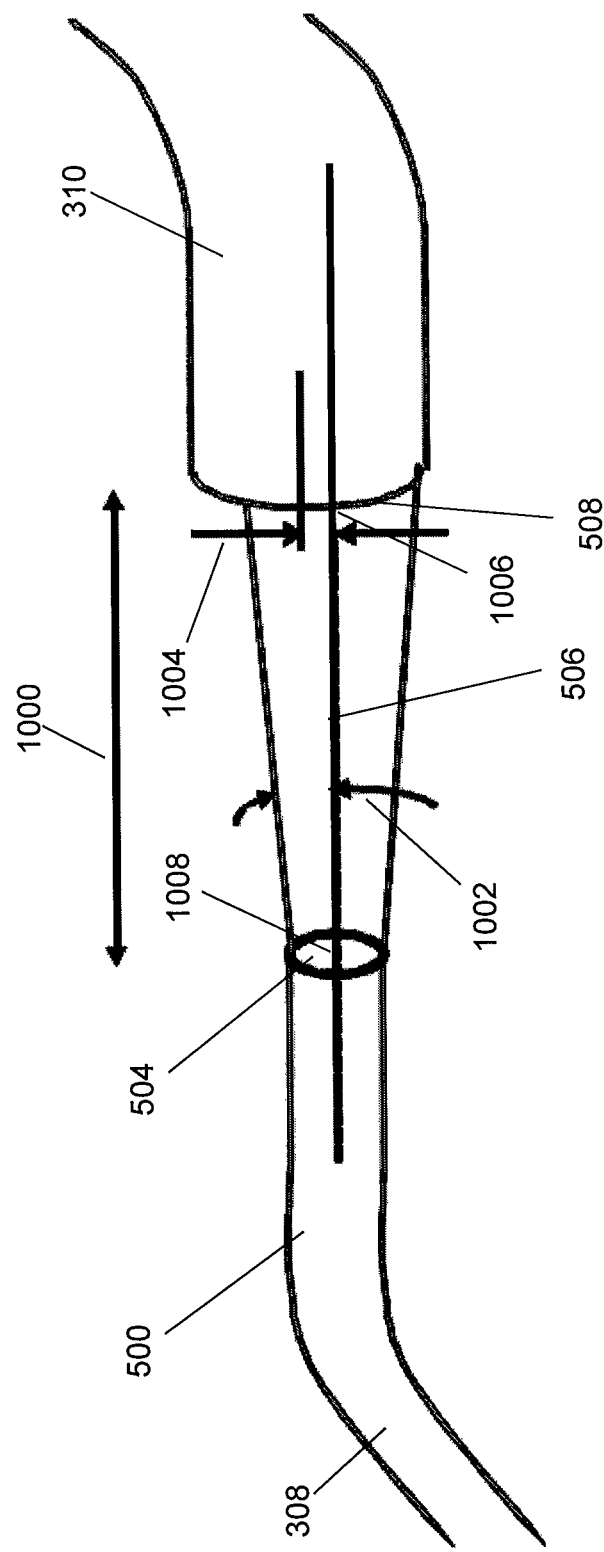
FIG. 10 depicts a diagram of a transmitting and a receiving optical fiber interface of the sensor of FIG. 3 in accordance with an illustrative embodiment.

With reference to FIG. 10, a diagram of the optical fiber interface of sensor 108 is shown in accordance with an illustrative embodiment without sample holder 206, which is mounted within the optical fiber interface as understood by a person of skill in the art. Actuator 314 may position exit face 504 of transmitting optical fiber 308 a maximum distance 1000 from entrance face 508 of receiving optical fiber 310. Transmitting optical fiber 308 is selected to generate a half-angle beam divergence 1002. Entrance face 508 of receiving optical fiber 310 is mounted to include a maximum offset 1004 of a center 1006 of entrance face 508 of receiving optical fiber 310 relative to a center 1008 of exit face 504 of transmitting optical fiber 308. Center 1006 of entrance face 508 of receiving optical fiber 310 and center 1008 of exit face 504 of transmitting optical fiber 308 are located on optical axis 506. To under-fill the entrance aperture of receiving optical fiber 310, the following condition is met:

$$r_1 + z\sin(\alpha)/n + \Delta r < r_2 \quad (4)$$

where $r_1$ is a core radius of transmitting optical fiber 308, $r_2$ is a core radius of receiving optical fiber 310, z is maximum distance 1000, $\alpha$ is half-angle beam divergence 1002 in the gap between transmitting optical fiber 308 and receiving optical fiber 310 in radians, $\Delta r$ is maximum offset 1004, and n is the refractive index of the sample deposited on sample holder 206. For small angles where $\sin\alpha \approx \alpha$, $\alpha$ and $\sin\alpha$ can be used interchangeably such that:

$$r_1 + z\alpha/n + \Delta r < r_2. \quad (5)$$

Thus, $$\alpha < \frac{n(r_2 - r_1 - \Delta r)}{z}. \quad (6)$$

The divergence condition expressed in equation (6) shows the beam divergence at the exit of transmitting optical fiber 308. In fiber optic systems, the fiber optics may be allowed to function as both the spatial and angular limiting apertures. The spatial aperture is defined by the radius of the fiber core. The angular aperture is defined by the refractive indices of the fiber core and cladding. A fiber optic will have a defined numerical aperture (NA), equal to $\sin\alpha$ in air. However, the NA of the fiber can exceed the limiting value of $\alpha$ given in equation (6). In this case, light rays accepted by transmitting optical fiber 308 and passed through the sample may over-fill receiving optical fiber 310. When this happens, the amount of light collected becomes susceptible to small changes in: 1) the misalignment of the optical fibers 308, 310 or $\Delta r$; 2) small changes in the spatial and angular distribution of light coming from light source 300, such as that which may result from use of LEDs; and 3) changes in path length z though spectrometer 102 may be designed to measure the transmission through the sample at a plurality of path lengths. Thus, for optimal stability and accuracy, transmitting optical fiber 308 may not be the sole limiting aperture of spectrometer 102.

It is well known that multimode optical fibers preserve, approximately, the angular distribution of rays that enter the optical fiber. Thus, the angular distribution through exit face 504 of transmitting optical fiber 308 can be limited by controlling the distribution of rays entering entrance face 502 of transmitting optical fiber 308. Thus, equation (6) may be used as a design formula for preparing the light entering transmitting optical fiber 308.

Figure 11:
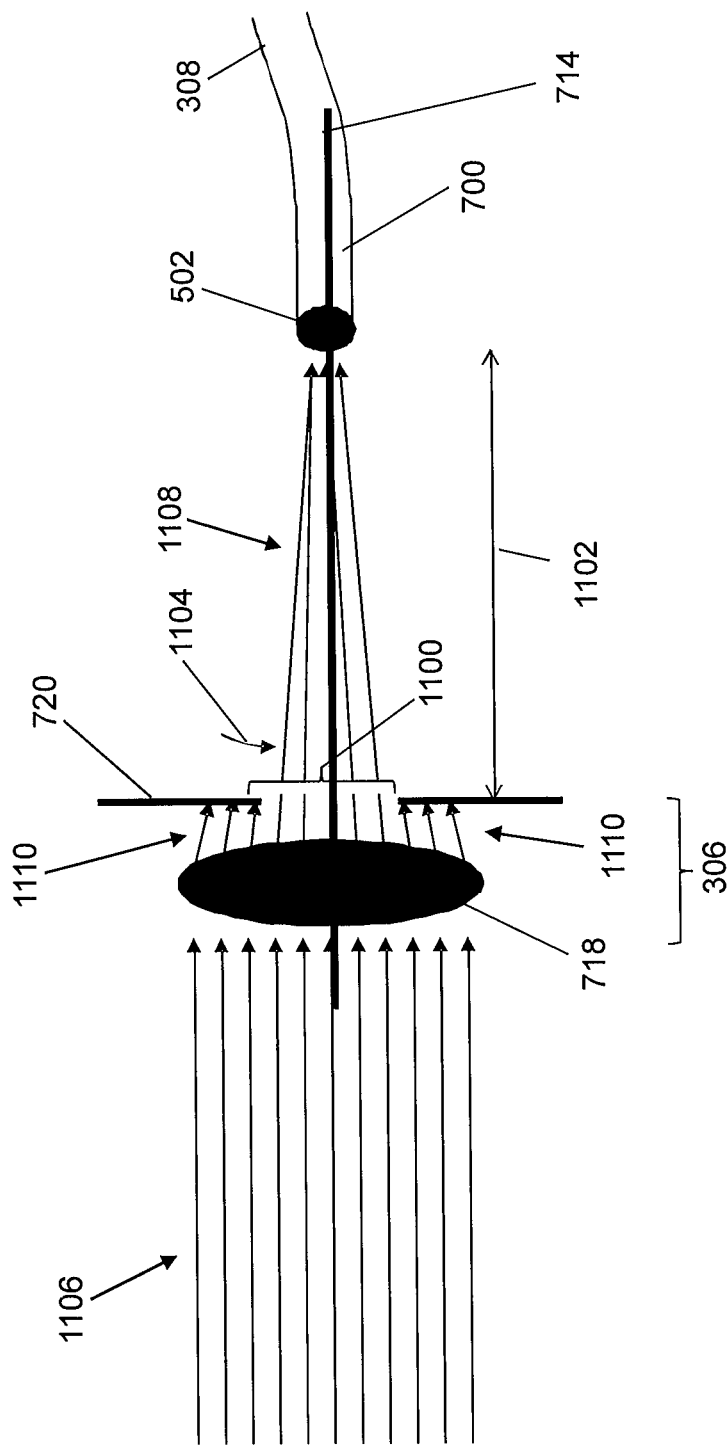
FIG. 11 depicts a diagram of a converging lens device and the transmitting optical fiber interface of the sensor of FIG. 3 in accordance with an illustrative embodiment.

With reference to FIG. 11, converging lens device 306 and entrance face 502 of transmitting optical fiber 308 are shown in accordance with an illustrative embodiment. Converging lens device 306 is positioned to receive light 1106 emitted along first axis 714 and to focus the received light spatially and angularly onto a portion of entrance face 502 of transmitting optical fiber 308. In the illustrative embodiment, converging lens device 306 includes converging lens 718 and aperture plate 720, which includes aperture 1100. Aperture plate 720 is positioned a distance 1102 from entrance face 502 of transmitting optical fiber 308 measured parallel to first axis 714.

Aperture 1100 allows a first portion 1108 of light 1106 to reach entrance face 502 of transmitting optical fiber 308 and blocks a second portion 1110 of light 1106 from reaching entrance face 502 of transmitting optical fiber 308. Thus, aperture 1100 is the opening that determines the half-angle 1104 of the angular distribution of first portion 1108 launched onto entrance face 502 of transmitting optical fiber 308.

Aperture 1100, which may be the diameter of converging lens 718, is positioned such that:

$$\alpha_s = r_s/z_s \quad (7)$$

where $\alpha_s$ is half-angle 1104 of the angular distribution of first portion 1108 and is also equal to $\alpha$ the half-angle beam divergence 1002 in the gap between transmitting optical fiber 308 and receiving optical fiber 310 in radians, $z_s$ is distance 1102, and $r_s$ is a radius of aperture 1100. Combining equations (6) and (7) results in a design formula for aperture 1100 that results in an underfilling of the entrance aperture of entrance face 508 of receiving optical fiber 310:

$$r_s \le z_s \frac{n(r_2 - r_1 - \Delta r)}{z} \quad (8)$$

As described, spectrometer 102 includes optical elements that limit the entrance aperture of light entering receiving optical fiber 310 to a value possibly significantly less than the numerical aperture of receiving optical fiber 310 by selecting half-angle 1104 to underfill the entrance aperture of entrance face 508 of receiving optical fiber 310 in both a spatial dimension and an angular dimension. The optical elements limit the aperture of light entering receiving optical fiber 310 such that at a given path length (z), the maximum diameter of light entering receiving optical fiber 310 is equal to or less than the core diameter of receiving optical fiber 310.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. An optical device comprising:
a converging lens device mounted to receive light from at least one light source that comprises: a first light source configured to emit first light approximately centered at a first wavelength, wherein the first wavelength is selected for analysis of the sample; a second light source configured to emit second light approximately centered at a second wavelength, wherein the second wavelength is selected for analysis of the sample, and further wherein the second wavelength is different from the first wavelength and from the baseline wavelength; a baseline light source configured to emit baseline light approximately centered at a baseline wavelength, wherein the baseline wavelength is different from the first wavelength and is selected to be centered in a region of the electromagnetic spectrum that is not used for analysis of the sample, wherein the received light is substantially collimated, and further wherein the converging lens device is configured to focus the received light onto a transmitting optical fiber; the transmitting optical fiber comprising an entrance face and an exit face, wherein the transmitting optical fiber is mounted to receive the focused light through the entrance face and to transmit the received, focused light from the exit face, through a sample and onto a receiving optical fiber;
a beamsplitter;
a reference detector, wherein the beamsplitter is mounted between the first light source and the converging lens device and is configured to reflect a baseline portion of the baseline light, a first portion of the first light, and a second portion of the second light towards the reference detector, wherein the reference detector is configured to generate a first reference signal indicating a first intensity of the first portion of the first light, a second reference signal indicating a second intensity of the second portion of the second light, and a third reference signal indicating a third intensity of the baseline portion of the baseline light;
a sample holder configured to hold the sample for analysis; and
the receiving optical fiber comprising an entrance face and an exit face, wherein the receiving optical fiber is mounted to receive the transmitted light through the entrance face of the receiving optical fiber after transmission through the sample, wherein the converging lens device is positioned to focus the received light onto the entrance face of the transmitting optical fiber such that a half-angle of the angular distribution of the focused light that reaches the entrance face of the transmitting optical fiber is selected to underfill an entrance aperture of the entrance face of the receiving optical fiber in both a spatial dimension and an angular dimension.

2. The optical device of claim 1, wherein the converging lens device comprises a converging lens, wherein a diameter of the converging lens is selected to allow a first portion of the focused light to pass through the converging lens and to reach the entrance face of the transmitting optical fiber, wherein the remainder of the focused light is blocked from reaching the entrance face of the transmitting optical fiber.

3. The optical device of claim 2, wherein the converging lens is positioned along an entrance optical axis of the transmitting optical fiber at a distance defined by $d_a/2\alpha_T$, where $d_a$ is the diameter of the converging lens and $\alpha_T$ is the half-angle of the angular distribution of the first portion of the focused light.

4. The optical device of claim 3, wherein a radius of a core portion of the entrance face of the transmitting optical fiber is selected to be less than or equal to $$r_2 - z\frac{\alpha_T}{n} - \Delta r,$$

where $r_2$ is a radius of the core of the entrance face of the receiving optical fiber, z is a maximum distance between the exit face of the transmitting optical fiber and the entrance face of the receiving optical fiber, n is a refractive index of the sample, and $\Delta r$ is a maximum offset of a center of the entrance face of the receiving optical fiber relative to an exit optical axis of the exit face of the transmitting optical fiber.

5. The optical device of claim 1, wherein the converging lens device comprises a converging lens and an aperture plate, wherein the aperture plate is mounted between the converging lens and the entrance face of the transmitting optical fiber and comprises an aperture configured to allow a first portion of the focused light to reach the entrance face of the transmitting optical fiber, wherein the aperture plate blocks the remainder of the focused light from reaching the entrance face of the transmitting optical fiber.

6. The optical device of claim 5, wherein the aperture plate is positioned along an entrance optical axis of the transmitting optical fiber at a distance defined by $d_a/2\alpha_T$, where $d_a$ is a diameter of the aperture and $\alpha_T$ is the half-angle of the first portion of the focused light.

7. The optical device of claim 6, wherein a radius of the core portion of the transmitting optical fiber is selected to be less than or equal to $$r_2 - z\frac{\alpha_T}{n} - \Delta r,$$

where $r_2$ is a radius of the core of the entrance face of the receiving optical fiber, z is a maximum distance between the exit face of the transmitting optical fiber and the entrance face of the receiving optical fiber, n is a refractive index of the sample, and $\Delta r$ is a maximum offset of a center of the entrance face of the receiving optical fiber relative to an exit optical axis of the exit face of the transmitting optical fiber.

8. The optical device of claim 1, wherein the light source further comprises a band limiting filter mounted between the first light source and the converging lens device, wherein the baseline light source is mounted to emit the baseline light towards the band limiting filter, and wherein the band limiting filter is further mounted to reflect the baseline light towards the converging lens device and to filter the first light emitted towards the converging lens.

9. The optical device of claim 1, wherein the light source further comprises a first band limiting filter mounted between the first light source and the converging lens device, wherein the second light source is mounted to emit the second light towards the first band limiting filter, and wherein the first band limiting filter is further mounted to reflect the second light towards the converging lens device and to filter the first light emitted towards the converging lens.

10. The optical device of claim 9, wherein the first band limiting filter is further mounted to reflect the baseline light towards the converging lens device.

11. The optical device of claim 10, wherein the light source further comprises a second band limiting filter mounted between the second light source and the baseline light source, wherein the baseline light source is mounted to emit the baseline light towards the second band limiting filter, and wherein the second band limiting filter is further mounted to reflect the baseline light towards the first band limiting filter and to filter the second light emitted towards the first band limiting filter.

12. The optical device of claim 1, further comprising:
wherein the beamsplitter is configured to reflect a baseline portion of the baseline light and a first portion of the first light towards the reference detector, wherein the reference detector is configured to generate a first reference signal indicating a first intensity of the first portion of the first light and a second reference signal indicating a second intensity of the baseline portion of the baseline light.

13. The optical device of claim 12, further comprising:
a detector coupled to receive the light from the exit face of the receiving optical fiber after transmission through the receiving optical fiber; and
an actuator operably coupled to adjust a distance between the exit face of the transmitting optical fiber and the entrance face of the receiving optical fiber;
wherein the detector is configured to generate a first sample signal indicating a first sample intensity of the first light for a first distance between the exit face of the transmitting optical fiber and the entrance face of the receiving optical fiber and to generate a second sample signal indicating a second sample intensity of the first light for a second distance between the exit face of the transmitting optical fiber and the entrance face of the receiving optical fiber.

14. The optical device of claim 13, wherein the detector is further configured to generate a third sample signal indicating a first sample intensity of the baseline light for the first distance and to generate a fourth sample signal indicating a second sample intensity of the baseline light for the second distance.

15. The optical device of claim 14, further comprising:
a processor; and
a computer-readable medium operably coupled to the processor, the computer-readable medium having computer-readable instructions stored thereon that, when executed by the processor, cause the optical device to
control the actuator to cause adjustment of the distance between the exit face of the transmitting optical fiber and the entrance face of the receiving optical fiber to the first distance;
generate the first sample signal;
generate the third sample signal;
control the actuator to cause adjustment of the distance between the exit face of the transmitting optical fiber and the entrance face of the receiving optical fiber to the second distance;
generate the second sample signal;
generate the fourth sample signal and
calculate an absorbance of the sample based on the first sample signal, the second sample signal, the third sample signal, and the fourth sample signal.

16. The optical device of claim 15, wherein the computer-readable instructions further cause the optical device to:
generate the first reference signal; and
generate the second reference signal;
wherein the absorbance of the sample is further calculated based on the first reference signal and the second reference signal.

* * * * *